United States Patent [19]

Miyamoto

[11] Patent Number: 5,196,340
[45] Date of Patent: Mar. 23, 1993

[54] ENZYME ELECTRODE CONTAINING AN ENZYME AND A COENZYME IMMOBILIZED IN SEPARATE LAYERS OF A MEMBRANE

[75] Inventor: Shigeyuki Miyamoto, Tokyo, Japan

[73] Assignee: NEC Corporation, Japan

[21] Appl. No.: 559,685

[22] Filed: Jul. 30, 1990

[30] Foreign Application Priority Data

Aug. 4, 1989 [JP] Japan .................................. 1-201208
Oct. 6, 1989 [JP] Japan .................................. 1-259988

[51] Int. Cl.$^5$ .................. C12M 1/40; C12N 11/04; C12Q 1/32; G01N 27/26
[52] U.S. Cl. .................................... 435/288; 435/26; 435/177; 435/182; 435/817; 204/403
[58] Field of Search .................... 435/14, 26, 174, 177, 435/180, 181, 182, 288, 817; 204/403

[56] References Cited

U.S. PATENT DOCUMENTS

| | | |
|---|---|---|
| 4,224,125 | 9/1980 | Nakamura et al. .............. 435/817 X |
| 4,415,666 | 11/1983 | D'Orazio et al. ................ 435/182 X |
| 4,418,148 | 11/1983 | Oberhardt ....................... 435/182 X |
| 5,057,421 | 10/1991 | Hofmann et al. ............... 435/817 X |

*Primary Examiner*—David M. Naff
*Attorney, Agent, or Firm*—Laff, Whitesel, Conte & Saret

[57] ABSTRACT

An enzyme electrode comprising an enzyme and a coenzyme immobilized in at least one layer is provided. This electrode has an outer membrane preventing the coenzyme from dissipation and so sensitivity and durability can be improved. In an inner membrane containing the enzyme and the coenzyme, a mediator of electron transfer may be added. The enzyme and the coenzyme may be separated in two layers, respectively, in the inner membrane to improve measurement sensitivity.

6 Claims, 4 Drawing Sheets

ENZYME ELECTRODE CONTAINING AN ENZYME AND A COENZYME IMMOBILIZED IN SEPARATE LAYERS OF A MEMBRANE

BACKGROUND OF THE INVENTION

1. Field of the Invention

The present invention relates to an enzyme electrode and more particularly an enzyme electrode containing an enzyme and a coenzyme as immobilized.

2. Description of the Prior Art

In order to determine concentration of a substance in a solution, it has been proposed to use an enzyme electrode comprising an enzyme, which is specifically reactive with the substance, that is, a substrate of the enzyme, and is immobilized on the surface of the electrode. According to its principle, the electrode is immersed in the solution to generate an enzyme reaction on the electrode surface and the amount of the reaction product is electrochemically detected, thereby to determine the concentration of the substance in the solution. Up to the present, enzyme electrodes using oxidation enzymes such as glucose oxidase have been proposed and produced.

On the other hand, some of oxidoreductases require existence of coenzymes. For example, dehydrogenases such as alcohol dehydrogenase and lactate dehydrogenase, which are industrially very useful, require existence of nicotinamide adenine dinucleotide (NAD) as a coenzyme. When these enzymes are applied to an enzyme electrode, it is necessary to detect a coenzyme derivative produced by the enzyme reaction, for example, reduced type NAD (NADH) in the case of the alcohol dehydrogenase, by the electrode to determine the amount of the substrate.

Heretofore, in most of such enzyme electrodes, only enzymes have been immobilized on the electrodes, and the coenzymes have been supplied from the solution without immobilization. For example, "Analytica Chimica Acta", 214 (1988), pp 161-172, discloses a report on an ethanol measurement system by a flow injection analysis method by means of a coenzyme solution. On the other hand, it has been proposed to immobilize an enzyme and a coenzyme at the same time on an electrode, by applying a coating of a solution containing an enzyme and a coenzyme on a carbon electrode, as described in the Japanese Patent Application Number 6961/1981.

Because a coenzyme solution is not stable enough to permit long time stock and is very expensive, it is not advantageous to supply the coenzyme from the solution. Further, the flow injection analysis method requires a large scale apparatus and so is not convenient for a case where simple measurement is desired. For these reasons, it is desirable to use an electrode on which both of an enzyme and a coenzyme are immobilized. The known electrode, on which the enzyme and the coenzyme are simply coated as above mentioned, however, has defects of low sensitivity owing to the fact that the coenzyme cannot be immobilized in a sufficiently large amount, and insufficient durability for repeated use owing to the fact that the coenzyme has strong tendency of dissipation into the solution because of its small size of molecule.

SUMMARY OF THE INTENTION

An object of the present invention therefore is to solve the problems of the prior art as described above and to present an enzyme electrode containing a coenzyme immobilized thereon in a stable manner and in a large amount together with an enzyme and having excellent measurement sensitivity.

Thus the present invention provides an enzyme electrode comprising:

(a) an electrode, (b) an inner membrane covering the electrode (a) and containing at least an enzyme and a coenzyme cooperative with the enzyme, which are immobilized in at least one layer, and (c) an outer membrane covering the inner membrane (b) and consisting essentially of a material which is difficult for the coenzyme to diffuse therein; whereby the coenzyme in the inner membrane (b) is prevented from dissipation.

As for the material of the outer membrane (c) of the enzyme electrode of the present invention, it is suitable to use a material having a small ratio of diffusion velocity of the coenzyme to diffusion velocity of the substrate specific to the enzyme and the coenzyme, for example, a bovine serum albumin (BSA) crosslinked with glutaraldehyde.

According to the present invention as above, the inner membrane (b) is covered with an outer membrane (c) in which the coenzyme is difficult to diffuse, and so it becomes possible to prevent the coenzyme in the inner membrane (b) from dissipation into the solution and thereby to keep coenzyme concentration in the inner membrane (b) at a high level. It becomes also possible thereby to improve measurement sensitivity of the enzyme electrode to the substrate and to enhance durability for repeated use and also fastness of the enzyme electrode.

It is possible to add a mediator of electron transfer, which catalyzes reaction between the coenzyme and the electrode, to the inner membrane (b) in order to increase velocity of the electron transfer reaction between them and to avoid any decrease of the measurement sensitivity caused when the reaction velocity is small.

It is also possible to separate the enzyme and the coenzyme in separate layers in the inner membrane (b), that is, in the form of an inner layer (b1) of an enzyme and an outer layer (b2) of a coenzyme. By this, it becomes possible to immobilize the enzyme and the coenzyme in higher concentrations on the electrode and so to highly improve the measurement sensitivity to the substrate and the durability for repeated use of the enzyme electrode. In effect, this enables to generate the enzyme reaction at a location closer to the electrode and so to catch a larger amount of the reduced coenzyme formed by the enzyme reaction by the electrode. The measurement sensitivity can thus be improved further on that score.

The shape of the electrode (a) is not limited and may be in the form of for example a wire, a plate, etc. The inner membrane (b) and the outer membrane (c) may envelope the wire form electrode (a) in the form of concentric layers. It is also possible to form the electrode (a), the inner membrane (b) and the outer membrane (c) on a base plate (d) in this order, whereby the electrode (a) and the inner electrode (b) are enclosed by the outer membrane (c) and the base plate (d).

The thickness of the outer membrane (c) in general should be selected from a range of 0.2-2 μm, in view of the various conditions of the enzyme, coenzyme and the substrate as used, the material and the density of the outer membrane, etc. If the thickness were less than 0.2 μm, it would be impossible to retain substances such as the coenzyme in the inner membrane (b). If the thickness were more than 2 μm, the diffusion velocity of the substrate would be much lowered and so the time required to achieve the steady-state current response would be much prolonged.

The thickness of the inner membrane (b) in general should be selected from a range of 1-25 μm. The thickness less than 1 μm would result in much reduction of the amounts of the enzyme, the coenzyme, etc. retained by the inner membrane (b) and so cause insufficient current response. The thickness more than 25 μm would also cause insufficient current response.

When the inner membrane (b) is separated into the inner enzyme layer (b1) and the outer coenzyme layer (b2), the thicknesses of these layers suitably are 0.5-15 μm and 0.5-10 μm, respectively. In general, it is preferable that the coenzyme layer (b2) is thinner than the enzyme layer (b1), since the coenzyme diffuses from the coenzyme layer (b2) into the enzyme layer (b1) wherein the reaction occurs. Further, in the measurement of substrate by an enzyme electrode, the substrate passes through the outer membrane (c) and the coenzyme layer (b2) and then reacts with the enzyme and the coenzyme, and so too much thickness of the coenzyme layer (b2) would cause insufficient current response as in the case of the outer membrane (c).

DESCRIPTION OF THE PREFERRED EMBODIMENTS

The present invention will be explained below further in detail with respect to its some embodiments shown as working examples.

EXAMPLE 1

An enzyme electrode was prepared as an embodiment of the present invention by using alcohol dehydrogenase as an enzyme and NAD as a coenzyme. As for a base plate of the enzyme electrode, a sapphire plate was used and a gold electrode of 3.52 mm² area was formed thereon by evaporating in accordance with a known method described in Japanese Patent Application No. 282,721/1988. To 15% BSA aqueous solution containing 2 U/μl alcohol dehydrogenase and 100 mM NAD, glutaraldehyde was added in an amount to give 0.5% concentration. This mixture was dropped on the electrode and spin-coated at 2,000 r.p.m. for 30 sec. to obtain an inner membrane of about 20 μm thickness after completing the crosslinking reaction at a room temperature. This spin-coating operation itself is known as described in a lift-off method for the preparation of enzyme membrane disclosed in Japanese Patent Application No. 209,165/1984. The obtained enzyme and coenzyme immobilized electrode was named as "Electrode-A".

Figure 1A:
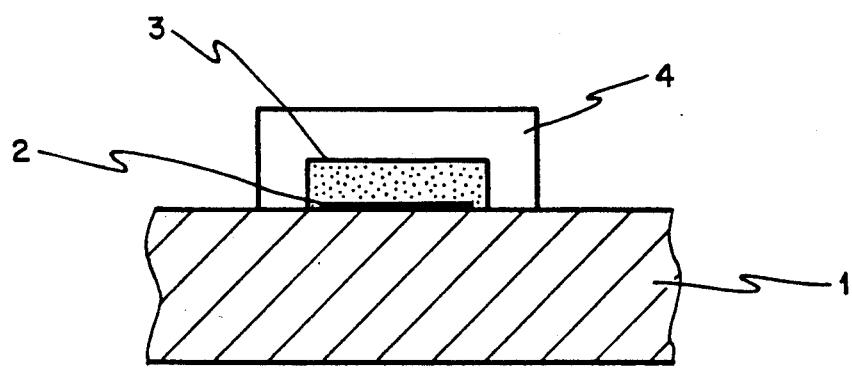
FIGS. 1(a), 1(b) and 1(c) respectively show cross sectional views of embodiments of the enzyme electrode of the present invention.

On the surface of the "Electrode-A", a coating by an outer membrane was provided. As for material of the outer membrane, polytetrafluoroethylene (PTFE), polyurethane, BSA crosslinked with glutaraldehyde were found usable. Particularly, the last mentioned BSA crosslinked with glutaraldehyde was excellent, since it was easy to prepare, it showed good adhesion to the electrode and it enabled to control transmission property by adjusting degree of the crosslinking. Hence, to 15% BSA aqueous solution, glutaraldehyde was added to give 5% concentration. This mixture was dropped on the electrode and spin-coated at 2,000 r.p.m. for 30 sec. to obtain an outer membrane of about 1 μm thickness. This electrode was named as "Electrode-B". As shown in FIG. 1(a), this "Electrode-B" comprises a base plate 1, an electrode 2, an inner membrane 3 wherein the enzyme and the coenzyme are immobilized and an outer membrane 4 to prevent dissipation of the coenzyme.

Figure 2:
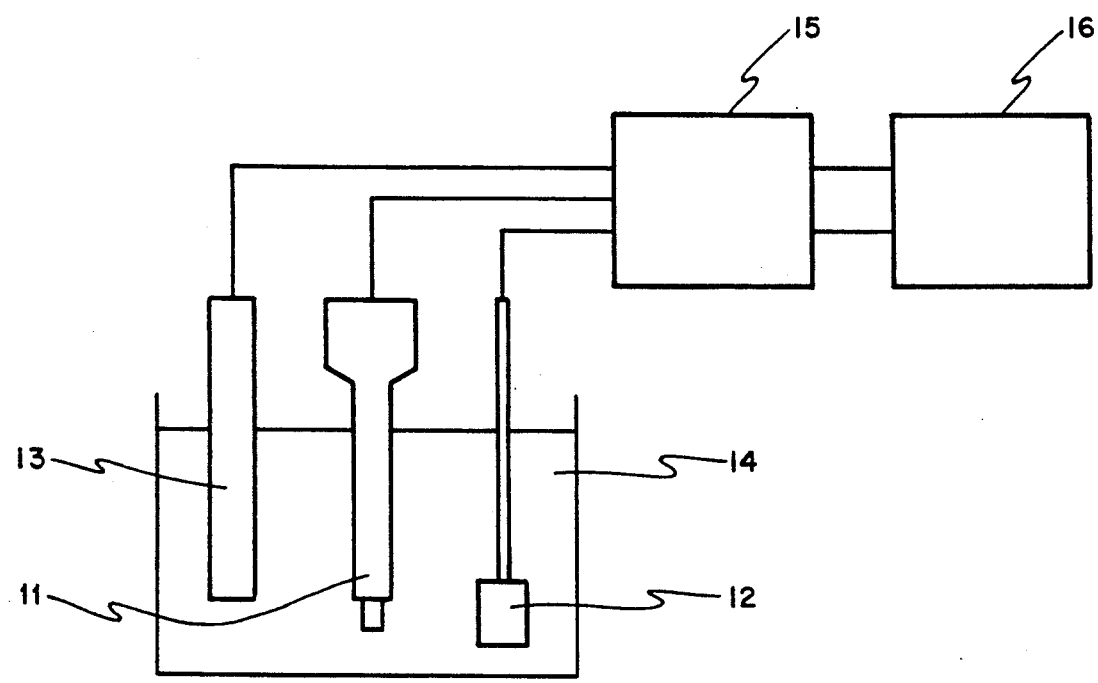
FIG. 2 shows a schematic illustration of an apparatus for determining ethanol concentration of a sample solution by means of an enzyme electrode.

As to these "Electrode-A" and "Electrode-B", current response to ethanol solution was measured by means of an apparatus shown in FIG. 2, wherein 11 indicates an enzyme electrode, 12 indicates a counter electrode, 13 indicates an Ag/AgCl reference electrode, 14 indicates a buffer solution containing ethanol, 15 indicates a potentiostat and 16 indicates a recorder. To the enzyme electrode 6, voltage of 0.75 V vs. Ag/AgCl reference electrode 13, which is required to oxidize NADH produced by the enzyme reaction, was applied, and variation of the current obtained was recorded.

Figure 3:
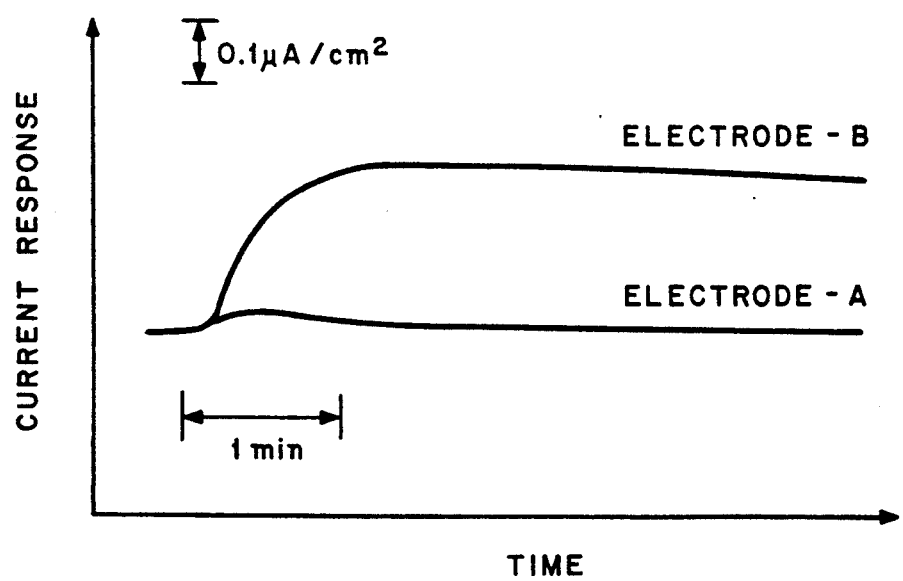
FIG. 3 shows a graphic illustration of current response to ethanol solution, determined by the electrode of FIG. 1(a) and an electrode of prior art by means of the apparatus of FIG. 2.

The current responses to 500 mM ethanol solution obtained by the "Electrode-A" and "Electrode-B" are shown in FIG. 3, from which it is understood that no sufficient current response could be obtained by the "Electrode-A" having no outer membrane owing to dissipation of the coenzyme, whereas sufficient current response could be obtained by the "Electrode-B" having the outer membrane.

Figure 4:
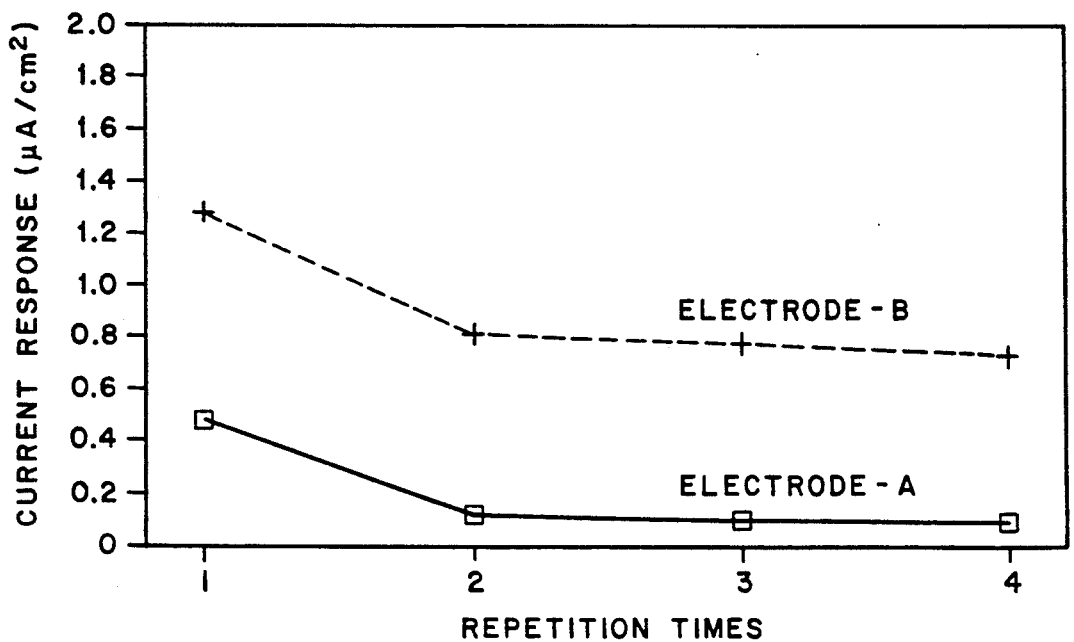
FIG. 4 shows a graphic illustration of decrease of the current response to ethanol solution when the electrode of FIG. 1(a) and an electrode of prior art are subjected to repeated use for the determination of the response.

FIG. 4 shows results of repeated measurements of the above 500 mM ethanol solution, to test decrease of current response as repetition time increases. In this FIG. 4, the line shown by square marks indicates the case of the "Electrode-A" and the line shown by plus marks indicates the case of the "Electrode-B". It is understood that almost no current response could be obtained by the "Electrode-A" having no outer membrane in the second and later times of measurements and so this "Electrode-A" could not be used for plural times of measurement, whereas the "Electrode-B" having the outer membrane could be used for plural times of measurement.

EXAMPLE 2

The procedures similar to those of the above Example 1 were followed, but together with the alcohol dehydrogenase and NAD, also a mediator of electron transfer, which works as an agent mediating electron transfer between NADH and the electrode, was immobilized. As for such mediator, it was found that potassium ferricyanide and Meldola's Blue were suitably usable. In this Example, the potassium ferricyanide was used.

Figure 1B:
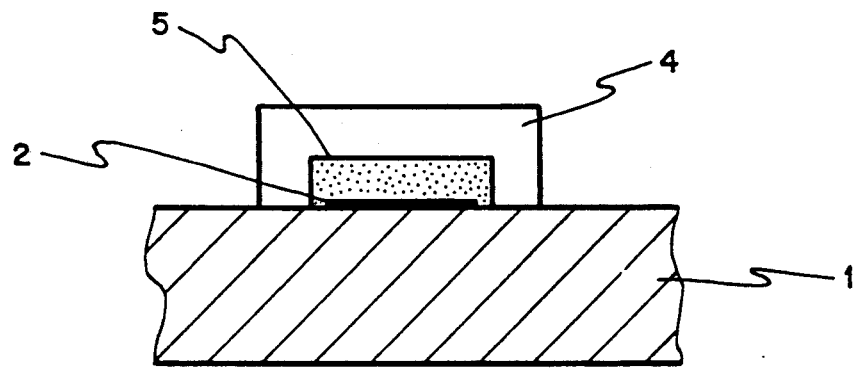

More particularly, to 15% BSA aqueous solution containing 2 U/μl alcohol dehydrogenase, 100 mM NAD and 100 mM potassium ferricyanide, glutaraldehyde was added to give 0.5% concentration. This mixture was dropped on a flat gold plate electrode and spin-coated at 2,000 r.p.m. for 30 sec. to obtain an inner membrane of about 20 μm thickness. Then 15% BSA aqueous solution containing 5% glutaraldehyde was dropped thereon and spin-coated at 2,000 r.p.m. for 5 sec. to form an outer membrane of about 1 μm thickness. This enzyme electrode having the mediator was named as "Electrode-C". As shown in FIG. 1(b), this "Electrode-C" comprises a base plate 1, an electrode 2, an inner membrane 5 wherein the enzyme, the coenzyme and the mediator are immobilized and an outer membrane 4 to prevent dissipation of the coenzyme.

Figure 5:
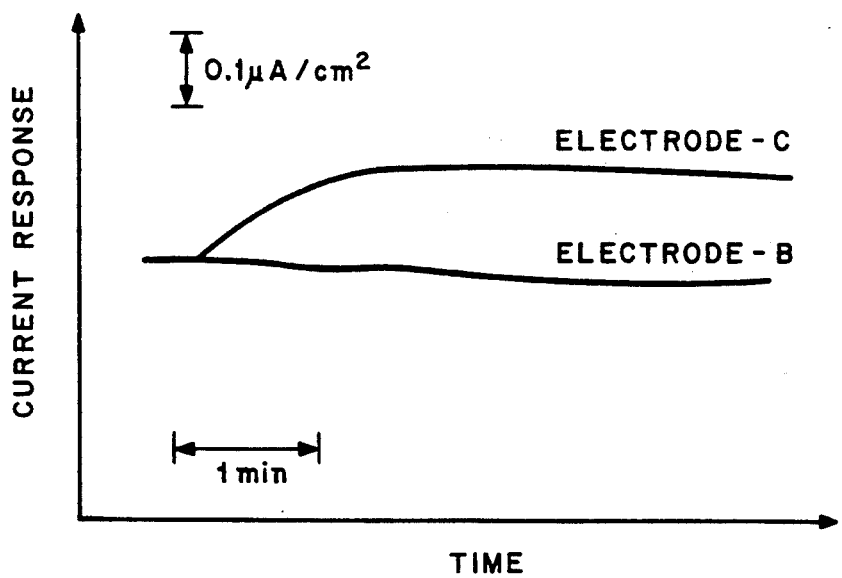
FIG. 5 shows a graphic illustration of current response to ethanol solution, determined by the electrode of FIG. 1(b) in comparison with that determined by the electrode of FIG. 1(a).

As to the "Electrode-C" and the "Electrode-B", current response to ethanol solution was measured by means of the apparatus shown in FIG. 2. The current responses to 500 mM ethanol solution obtained by these electrodes when voltage of 0.3 V vs. Ag/AgCl reference electrode was applied thereto are shown in FIG. 5, from which it is understood that the "Electrode-C" having the immobilized potassium ferricyanide as the mediator of electron transfer between NADH and the electrode enables to obtain sufficient current response to ethanol solution even at a low voltage level and hence to further improve the measurement sensitivity.

EXAMPLE 3

The procedures similar to those of the above Example 1 were followed, but the inner membrane was formed by two separate layers respectively of the enzyme and the coenzyme, formed on the electrode in this order.

More particularly, to 15% BSA aqueous solution containing 2 U/μl alcohol dehydrogenase, glutaraldehyde was added to give 0.5% concentration. This mixture was dropped on the gold electrode formed as in the Example 1, spin-coated at 2,000 r.p.m. for 30 sec. and crosslinked at room temperature for 2 hrs. to form an enzyme immobilized layer of about 12 μm thickness.

Next, to 15% BSA aqueous solution containing 100 mM NAD, glutaraldehyde was added to give 0.5% concentration. This mixture was dropped on the above enzyme immobilized layer, spin-coated at 2,000 r.p.m. for 30 sec. and crosslinked at room temperature for 2 hrs. to form a coenzyme immobilized layer of about 6 μm thickness.

Figure 1C:
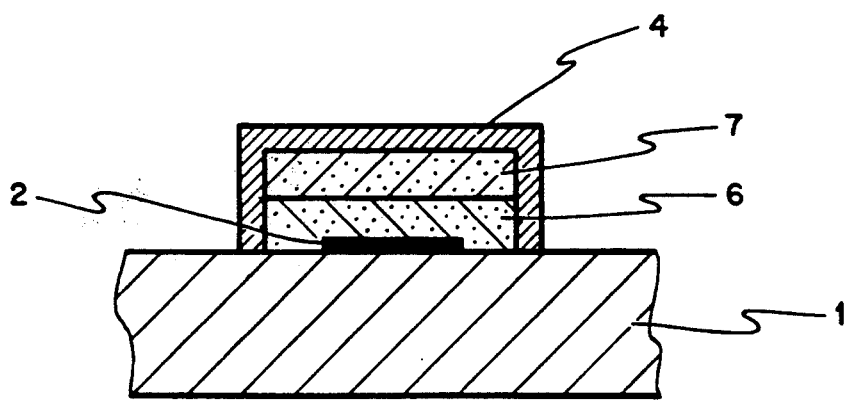

Finally, an outer membrane was formed on the coenzyme immobilized layer as in the Example 1 to form an enzyme electrode. This enzyme electrode having separate layers of enzyme and coenzyme was named as "Electrode-D". As shown in FIG. 1(c), this "Electrode-D" comprises a base plate 1, an electrode 2, an enzyme immobilized layer 6, a coenzyme immobilized layer 7 and an outer membrane 4 to prevent dissipation of the coenzyme.

Figure 6:
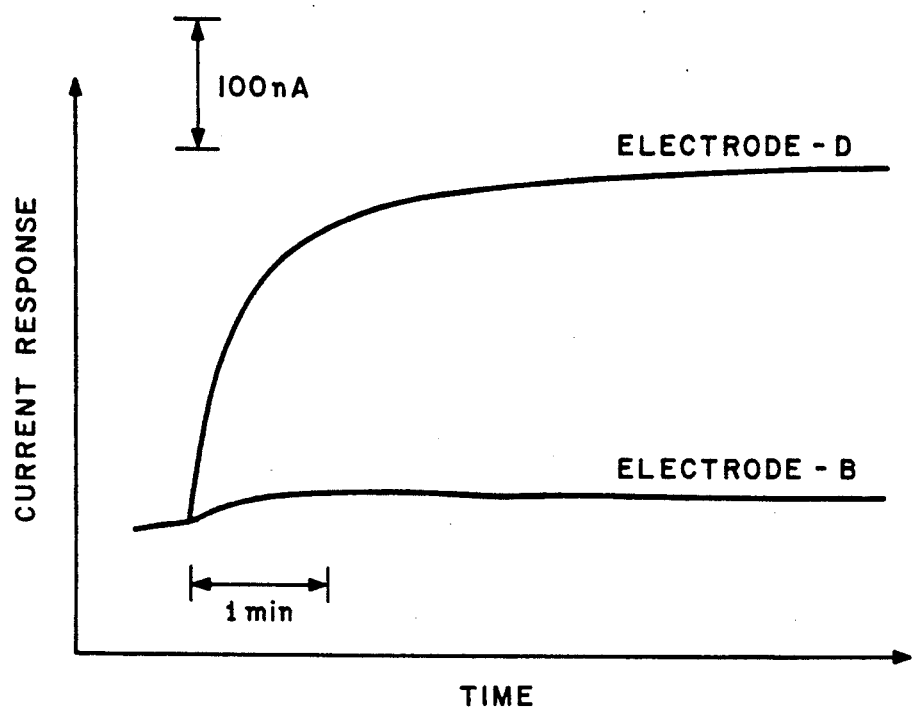
FIG. 6 shows a graphic illustration similar to FIG. 5, but determined by the electrode of FIG. 1(c) in comparison with that determined by the electrode of FIG. 1(a).

FIG. 6 shows current responses to 500 mM ethanol solution obtained by the "Electrode-D" and the "Electrode-B" in the measurement as in the Example 1. It is understood from this FIG. 6 that the "Electrode-D" having enzyme and coenzyme immobilized in separate layers gives much larger current response than the "Electrode-B" having enzyme and coenzyme in the same layer and thus has much improved measurement sensitivity.

Figure 7:
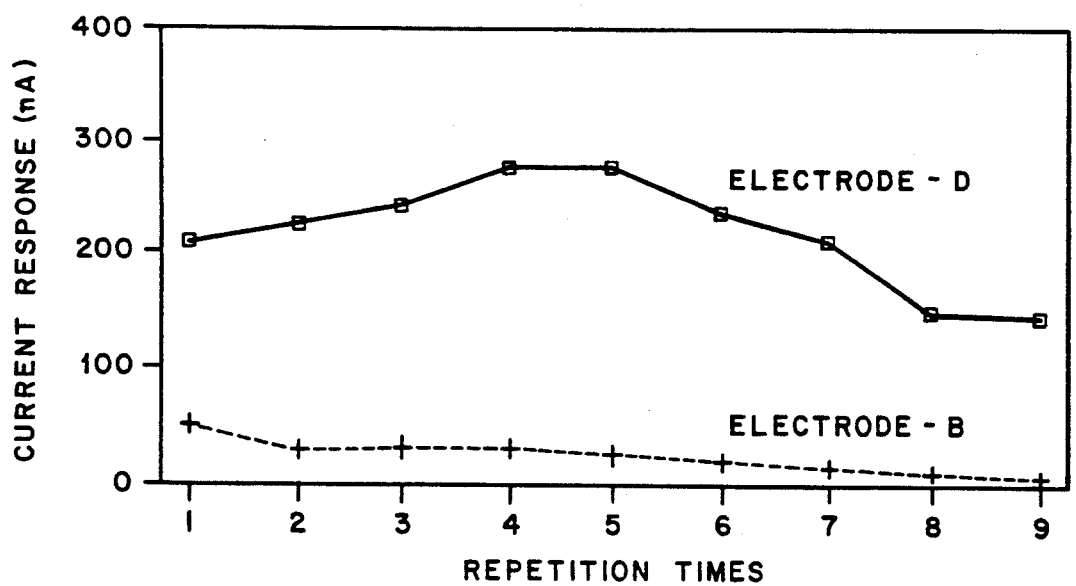
FIG. 7 shows a graphic illustration similar to FIG. 4, but when the electrodes of FIGS. 1(a) and 1(c) are used.

FIG. 7 shows results of repeated measurements of the above 500 mM ethanol solution to test decrease of current response as repetition time increases. In this FIG. 7, the line shown by square marks indicates the case of the "Electrode-D" and the line shown by plus marks indicates the case of the "Electrode-B". It is understood from this FIG. 7 that the "Electrode-D" has much improved durability for repeated use of more than 10 times, since both of enzyme and coenzyme are immobilized in larger amounts and in more active state when compared with the "Electrode-B".

As explained in detail as above, the present invention has enabled to improve the measurement sensitivity and the durability for repeated use of an enzyme electrode by providing an outer membrane preventing the coenzyme from dissipation into the sample solution. This outer membrane can be used to immobilize a mediator of electron transfer together with the coenzyme in the inner membrane or to immobilize the enzyme and the coenzyme in separate layers in the inner membrane, to further improve the measurement sensitivity and the durability for repeated use.

I claim:

1. An enzyme electrode comprising:
   (a) an electrode;
   (b) an inner membrane covering the electrode (a), said inner membrane comprising two separate layers comprising an inner layer in which an enzyme is immobilized and an outer layer in which a coenzyme which is cooperative with the enzyme is contained, and
   (c) an outer membrane covering the inner membrane (b) and consisting essentially of a material which is difficult for the coenzyme to diffuse therein; whereby the coenzyme in the inner membrane (b) is prevented from dissipation.

2. The enzyme electrode according to claim 1, wherein the outer membrane consists essentially of bovine serum albumin (BSA) crosslinked with glutaraldehyde, polytetrafluorethylene (PTFE) or polyurethane.

3. The enzyme electrode according to claims 1 or 2, wherein the enzyme is alcohol dehydrogenase or lactate dehydrogenase and the coenzyme is nicotinamide adenine dinucleotide (NAD).

4. The enzyme electrode according to claim 1, wherein the electrode (a), the inner membrane (b) and the outer membrane (c) are formed on a base plate (d) in this order; whereby the electrode (a) and the inner membrane (b) are enclosed by the outer membrane (c) and the base plate (d).

5. The enzyme electrode according to claim 1, wherein the outer membrane is of the thickness in the range of 0.2-2 μm.

6. The enzyme electrode according to claim 1, wherein the inner enzyme layer is of the thickness in the range of 0.5-15 μm and the outer coenzyme layer is of the thickness in the range of 0.5-10 μm.

* * * * *